United States Patent [19]
Jeffcoat

[11] Patent Number: 5,766,009
[45] Date of Patent: Jun. 16, 1998

[54] ELASTICALLY STABILIZED ENDOSSEOUS DENTAL IMPLANT

[76] Inventor: Robert L. Jeffcoat, 2109 Country Ridge La., Vestavia Hills, Ala. 35243

[21] Appl. No.: 376,013

[22] Filed: Jan. 20, 1995

[51] Int. Cl.⁶ .................................................. A61C 8/00
[52] U.S. Cl. ................................................... 433/173
[58] Field of Search ............................. 433/172, 173, 433/174, 175, 176

[56] References Cited

U.S. PATENT DOCUMENTS

| | | | |
|---|---|---|---|
| 2,721,387 | 10/1955 | Ashuckian | 32/10 |
| 2,857,670 | 10/1958 | Kiernan | 32/10 |
| 3,435,526 | 4/1969 | Brancato | 433/174 |
| 3,497,953 | 3/1970 | Weissman | 32/10 |
| 4,523,587 | 6/1985 | Frey | 433/173 |
| 4,738,062 | 4/1988 | Dickey | 52/157 |
| 4,773,858 | 9/1988 | Marquez | 433/173 |
| 4,854,873 | 8/1989 | Linden | 433/173 |
| 5,013,242 | 5/1991 | Prezmecky | 433/174 |
| 5,076,788 | 12/1991 | Niznick | 433/173 |
| 5,174,755 | 12/1992 | Fukunda | 433/173 |
| 5,207,679 | 5/1993 | Li | 606/72 |
| 5,213,500 | 5/1993 | Salazar et al. | 433/173 X |
| 5,217,486 | 6/1993 | Rice et al. | 606/232 |
| 5,439,381 | 8/1995 | Cohen | 433/177 X |
| 5,468,150 | 11/1995 | Brammann | 433/173 |

FOREIGN PATENT DOCUMENTS

| | | |
|---|---|---|
| 0 024 008 | 7/1980 | European Pat. Off. . |
| 3643219 | 6/1988 | Germany . |
| 1373401 | 2/1899 | Russian Federation . |

*Primary Examiner*—Nicholas D. Lucchesi
*Attorney, Agent, or Firm*—Needle & Rosenberg, P.C.

[57] ABSTRACT

A dental prosthesis comprising an anchoring base for insertion into prepared osseous tissue is provided. The anchoring base generally has a body portion having a top, a bottom, and an outside surface. A crown portion is provided for attachment to the top of said anchoring base. Provided is an outside surface for enhanced osteointegration of said tissue to said anchoring base and an elastic member extending outwardly from the outside surface of said body portion to provide a stabilizing force against said living osseous tissue. The outside surface of the body portion can be provided with a recess for selectively receiving the elastic member. The elastic member can extend outwardly from the outside surface of said body portion or be selectively retained within the corresponding recess. The elastic member can be made of a biodegradable material. The biodegradable materials used in the implant can further incorporate bioactive agents which are gradually released into the surrounding tissue.

30 Claims, 3 Drawing Sheets

ELASTICALLY STABILIZED ENDOSSEOUS DENTAL IMPLANT

FIELD OF THE INVENTION

The present invention relates to the field of dental prostheses. In particular, the invention relates to the field of endosseous dental implants with stabilizing members.

BACKGROUND OF THE INVENTION

Endosseous dental implants rely upon the growth of bone tissue in and around the implant, a process called osseointegration. Most endosseous dental implants take advantage of osseointegration to create a long-lasting mechanical union between the artificial implant and the natural supporting bone. Two primary bonding mechanisms, separately or together, can effectuate such osseointegration: microscopic bonding between the bone tissue and the implant surface; and macroscopic ingrowth of bone into interstices of the implant to create a mechanical locking effect.

Successful osseointegration requires that the implant and bone tissue be brought into close proximity to one another, and held thus for a substantial time period, usually several months to a year, undisturbed by relative motion, fluctuating loads, or microbiological assault. Therefore, following placement, the wound is preferably closed over the implant to protect it from infection during an unloaded healing period. After several months of osseointegration, the implant is again surgically exposed, and prosthetic devices are attached.

In most existing implant systems, the necessary stabilization is achieved by pressing the implant into a closely fitting prepared socket or, in the case of some "rootform" implants, screwing a threaded implant into a tapped bone site. Many alterations to the surface profile have been offered in the context of osseointegrated implants, such as variations on protruding helical threads. Other researchers have addressed ways to improve mechanical stabilization. A variety of mechanical locking mechanisms, such as barbs, spurs, legs, pins, screws, spiders, cams, etc. have been developed, often without reference to their applicability to osseointegration.

The disadvantages of present dental implants known to skilled clinicians are many. The tissue site preparation for an osseointegrated implant is highly demanding, because the preparation must be correctly sized, placed, and angled in accordance with a treatment plan and the dimensions of the proposed implant. The requirement for mechanical stabilization places close tolerances, by surgical standards, on the diameter of the tissue preparation site. If a threaded implant is used, the bone, which is frequently thin and weak in patients needing implants, must be tapped to receive it. These preparatory procedures must be done with special low-speed drilling equipment to avert frictional heating and necrosis of the bone tissue. As a result, implant success is highly dependent on the practitioner's skill and the condition of the patient. Furthermore, conventional rootform implants rely on the presence of sound bone surrounding a substantial portion of their surface, making them inappropriate for many of the patients who need them most.

In attempts to provide additional stabilization for dental implants, the barbs and similar protrusions provided by some current implant designs may cause long-term discomfort, instability, resorption or infection to patients and interfere with the process of osseointegration, due to the permanence of the protrusions from the implant into the surrounding tissues for the life of the implant. Additionally, the design of existing dental implants with such anchoring protrusions causes unnecessary and deleterious tearing and collateral damage to the surrounding tissues during the process of inserting the implant into the patient.

The relatively high cost of dental implants is due in large part to the time and skill needed to place them, and to the possibility of future complications. A design which allows reliable results to be achieved without requiring precision site preparation and recurring office visits would improve productivity and lower costs.

SUMMARY OF THE INVENTION

The present invention provides an osseointegrated dental implant employing elastic members primarily for stabilization of the implant during healing, and secondarily for resisting disruptive forces throughout the life of the implant. The invention also provides a means for positioning the dental implant which minimizes tissue damage to the patient. The present invention provides an osseointegrated dental implant with recessed grooves for receiving therein the elastic stabilizing members for positioning the implant, which minimizes tissue damage to the patient during the implantation procedure. The invention further provides a retention means for maintaining the elastic stabilizing members within the recessed grooves during placement of the implant. The invention provides that such a retention means comprises a polymer matrix being adapted to biodegrade, or reabsorb, over a predetermined period of time, wherein said polymer matrix is disposed about said received elastic members. Alternatively, the invention provides a retention means comprising a retention pin adapted to be removably disposed about said received elastic members.

The present invention also provides an osseointegrated dental implant which employs an elastic stabilizing member which biodegrades, or reabsorbs, over another predetermined period of time. The invention also provides such osseointegrated dental implants with a variety of shapes of biodegradable elastic stabilizing members.

The invention also provides for the incorporation of bioactive agents, or medicaments, into one or more of the biodegradable elements, from which said agents or medicaments may be released in a gradual and controlled fashion into the proximity of surrounding tissues.

Therefore, it is an object of the present invention to provide an osseointegrated dental implant with recessed grooves for receiving therein the elastic stabilizing members.

It is a further object of the invention to provide a retention means for maintaining the elastic stabilizing members within the recesses grooves during placement of the implant.

It is also an object of the present invention to provide an osseointegrated dental implant employing elastic stabilizing members which naturally dissolve, or biodegrade, over a period of time.

It is a further object of the present invention to provide osseointegrated dental implants with a variety of shapes of biodegradable elastic stabilizing members.

It is yet a further object of the present invention to permit the controlled release of bioactive agents or medicaments from within biodegradable polymer elements of the implant into the surrounding tissues. These and other objects of the invention will be apparent to one skilled in the art with reference to the detailed embodiments described herein.

BRIEF DESCRIPTION OF THE FIGURES

FIG. 3C also shows a tool which is used for the insertion of the dental implant into the tissue site.

DETAILED DESCRIPTION OF THE INVENTION

Figure 1:
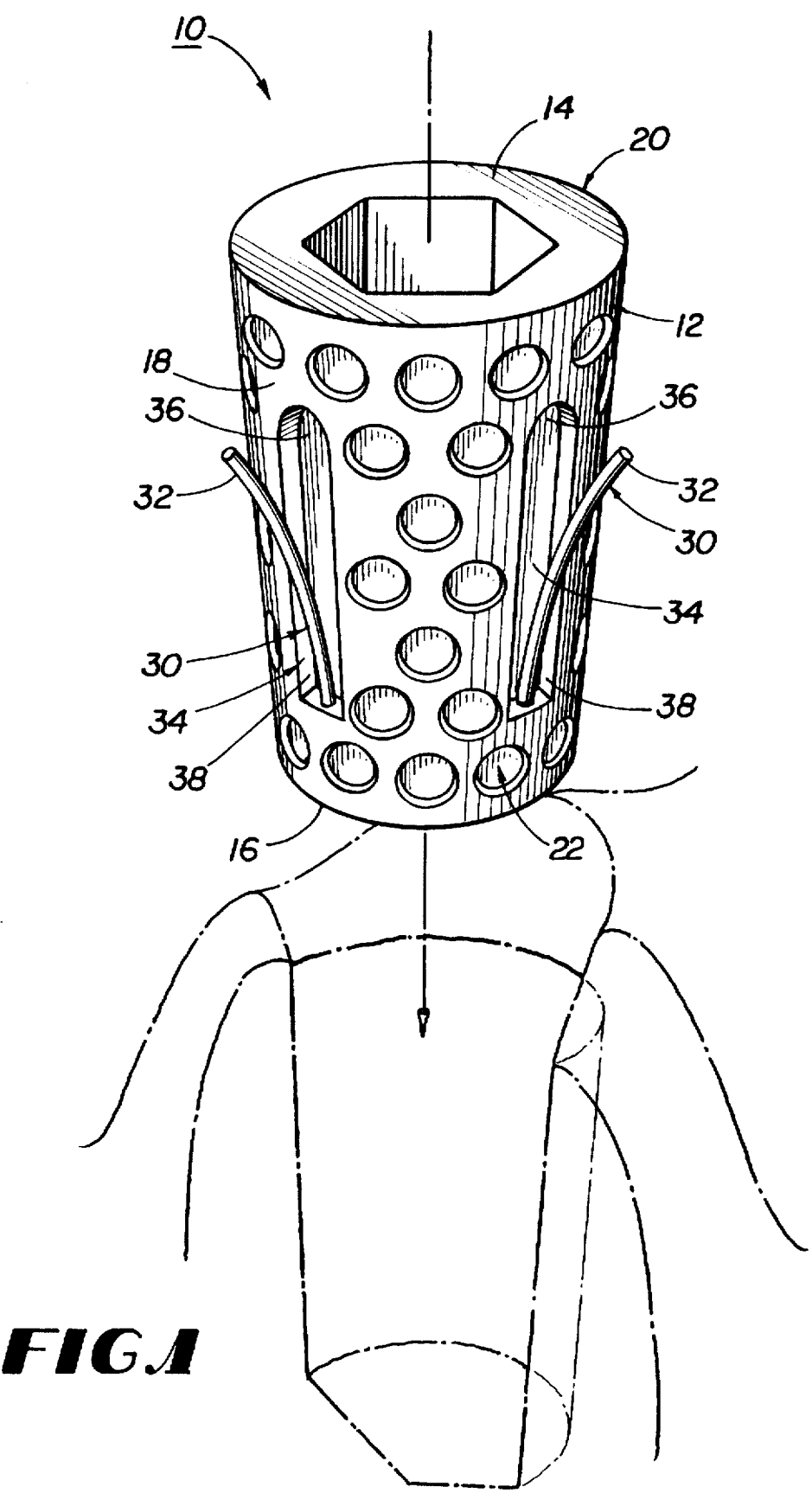
FIG. 1 is a perspective view of one embodiment of the dental implant of the present invention.

As seen in FIG. 1, the invention provides a dental prosthesis that has an anchoring base 10 for insertion into prepared osseous tissue. The anchoring base 10 generally has a body portion 12 having a top 14, a bottom 16, and an outside surface 18, a means 20 for attaching the top 14 of said anchoring base 10 to a crown portion (not shown), a means 22 on the outside surface 18 of said anchoring base 10 for enhancing osteointegration of said tissues to said anchoring base 10, and an elastic member 32 extending outwardly from the outside surface 18 of said body portion 12 to provide a stabilizing force against said living osseus tissues. As shown in FIG. 1, an implant constructed in accordance with the invention can have more than one elastic member 32 protruding from its outside surface 18.

In use, the implant is inserted into the prepared site by suitable means. In a preferred embodiment, a tapered anchoring base 10 is simply pressed directly into a similarly shaped and prepared site in the maxilla or mandible until it is seated. The elastic members 32 are then deployed, if necessary, so as to bear against the sides of the prepared implant site. Subsequent steps in the surgical procedure and completion of the prosthesis are unchanged from current practice.

In the embodiment shown in FIG. 1, the means 20 for attaching the top 14 of the anchoring base 10 to the crown portion (not shown) is an opening in the top 14 of said body portion 12 adapted to attachably receive a corresponding or complimentary shaped projection on said crown portion. However, the top 14 of said body portion 12 can be threaded to receive complimentary threads on the projection on said crown portion such that said crown portion can be removably attached to said anchoring base 10.

The means 22 on the outside surface 18 of the anchoring base 10 for enhancing osteointegration of living tissues can be a variety of features, such as rings, grooves, pores, dimples, waffles, slots, etc. to facilitate microscopic bonding or macroscopic bone ingrowth.

Figure 4:
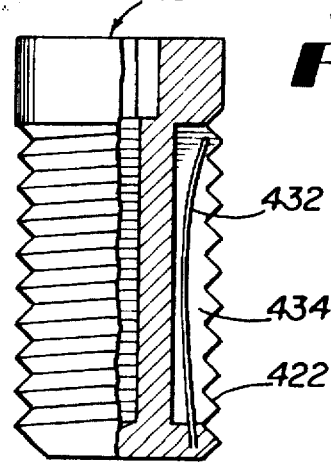
FIG. 4 is a partial cross-section view showing an alternative embodiment of the means for enhancing osteointegration of the dental implant.

The osteointegration enhancing means 22 on the outside surface 18 can be for example, sputtered metallic coatings (e.g., titanium) or bioactive coatings (e.g., hydroxyapatite). The implant can be generally cylindrical or tapered in vertical cross-section, or can be a blade-type or other non-circular geometries. For example, FIG. 1 shows an embodiment wherein the osteointegrating means 22 is numerous indentations on the outside surface 18 of the implant base 10, and FIG. 4 shows an alternative embodiment of the invention where the osteointegrating means 422 on the base 410 is a threaded or ribbed surface.

In the embodiment shown in FIG. 1, the anchoring base 10 can have a recess 34 in the outside surface 18 of said body portion 12 for selectively receiving said elastic member 32 therein during positioning of said body portion 12 of said dental prosthesis into said tissues. By "positioning" it is meant that the elastic member 32 may be retained in the recess 34 during the surgical procedure and for a time following the procedure to be determined by the dentist. When a plurality of elastic members 32 are used, each can have a corresponding recess 34. The recess 34 provides a space into which the elastic member 32 can be depressed or held to facilitate placement and adaptation into the tissue site with a minimum of collateral tissue damage caused by an otherwise extending elastic member 32.

The recess 34 has an upper end 36 and a lower end 38. It should be noted that the elastic member 32 can be attached to the body portion 12 within the recess 34 adjacent either the upper end 36 or the lower end 38, or may be attached to the outside surface 18 of the body portion 12 adjacent the recess 34.

Figure 2A:
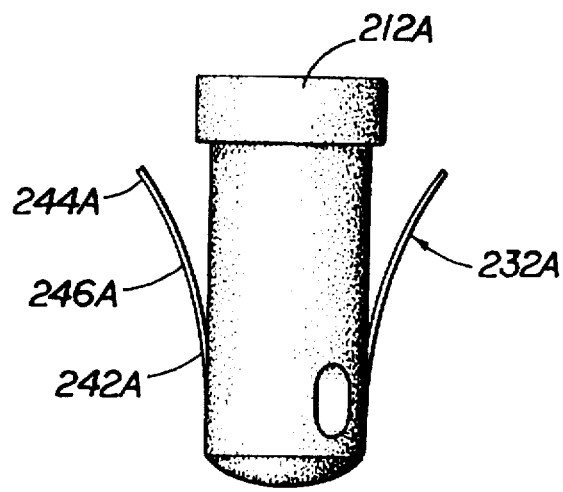
FIGS. 2A–2C are side views showing three alternative embodiments for the stabilizing elastic members of the dental implant of the present invention.
Figure 2B:
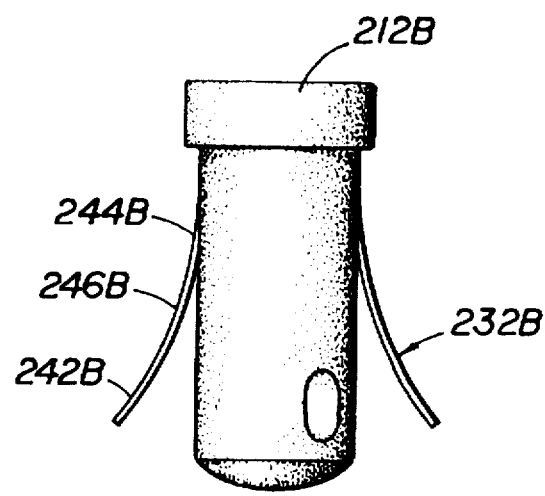
Figure 2C:
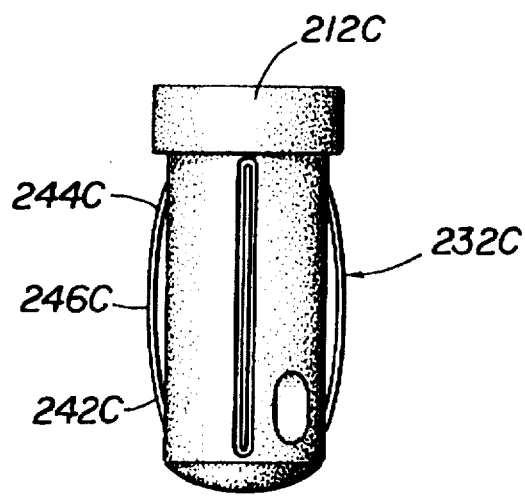

As seen in FIGS. 2A–C, the elastic member 232A–C comprises a bottom end 242, a top end 244A–C and a middle portion 246A–C. In the embodiment of FIG. 2A, the bottom end 242A of the elastic member 232A is attached to the body portion 212A and the top end 244A extends outwardly from said body portion 212A. This results in a convex coronal shape to the middle portion 246A of the elastic member 232A, which resists extractive forces in addition to stabilizing the implant centrally. In another embodiment of FIG. 2B, the top end 244B of the elastic member 232B is attached to the body portion 212B and the bottom end 242B extends outwardly from the body portion 212B. This results in a convex apical shape to the middle portion 246B of the elastic member 232B, which especially resists occlusal forces. In another embodiment of FIG. 2C, either the bottom end 242C or the top end 244C of the elastic member 232C is attached to said body portion 212C, the other end being free but disposed within the recessed grove, and the middle portion 246C of the elastic member 232C extends outwardly from said body portion 212C. This results in a convex arcuate shape to the middle portion 246C of the elastic member.

The detailed shape and placement of the stabilizing elastic members are significant to the initiation of the osseointegration process. Although the described elastic members are specified, other configurations, such as a helix wound around the implant, are possible and may be desirable. When the elastic member is not constructed of a resorbable biodegradable material, a material with good elastic memory and biocompatibility properties can be used, such as Nitinol alloy, or ordinary (e.g. stainless) metals, ceramics or other nonmetals.

Figure 3A:
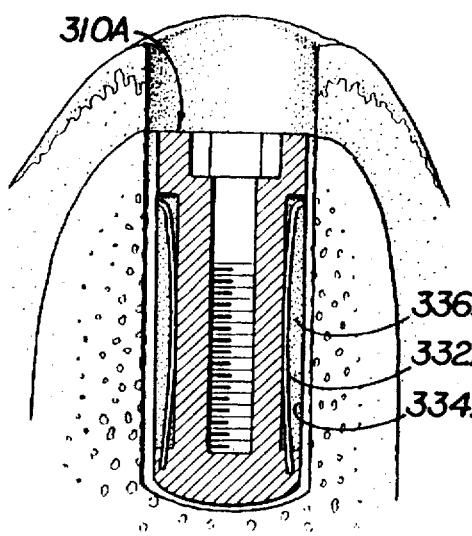
FIGS. 3A–3C are partial cross-section views showing alternative embodiments of the elastic member retaining means of the dental implant of the present invention within a prepared tissue site.

As shown in the preferred embodiment in FIG. 3A, the anchoring base 310A of the dental prosthesis further has a retention means 336A for selectively maintaining the elastic member 332A within the corresponding recess 334A. The retention means 336A can be constructed of a polymer matrix being adapted to biodegrade over a predetermined period of time, wherein said polymer matrix is temporarily disposed about said received elastic member 332A to temporarily maintain said elastic member 332A within said recess 334A. Therefore, in the embodiment shown in FIG. 3A the elastic member 332A is partially embedded within the polymer matrix retention means 336A. In other preferred embodiments, the dental prosthesis can have an elastic member 32, 232 itself also constructed of biodegradable polymer.

The biodegradable polymer of the implant stabilizing elastic members 32, 232 or the biodegradable retention means 336A for selectively maintaining the elastic member 332A within the corresponding recess 334A can be constructed of a biodegradable, or reabsorbable, polymer component such as polyglycolide, polylactide or polycaprolactone, or a combination thereof. The biodegradable polymer can be constructed with various polymeric formulations and relative amounts of these and other components to achieve a desired predetermined period of time over which the material will degrade. Such particular polymers may be obtained from Birmingham Polymers, Inc. (Birmingham, Ala.).

For example, when the biodegradable, or reabsorbable, polymer is to be used for the construction of an elastic member stabilizing means 32, 232 the predetermined period for biodegradation is preferably 3 to 12 months. When the biodegradable, or reabsorbable, polymer is to be used for the construction of an elastic member retaining means 336A for the positioning of the implant, the predetermined period for biodegradation and release of the elastic member 332A from the recess 334A is preferably several hours.

Figure 3B:
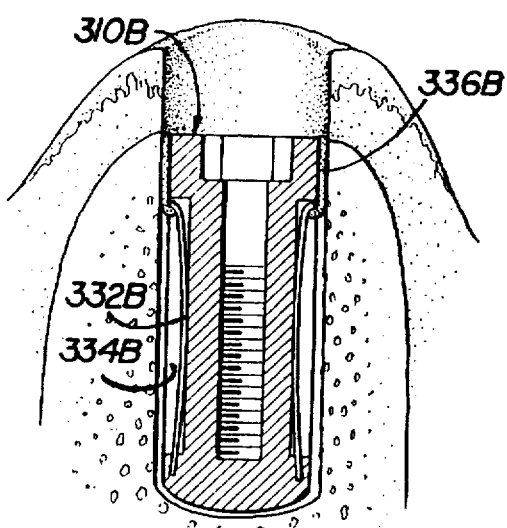

In another embodiment shown in FIG. 3B, the retention means 336B further comprises one or more retention pins adapted to be removably disposed about said received elastic member 332B to temporarily maintain said elastic member 332B within said recess 334B during insertion of said prosthesis into said tissues. The retention pin retention means 336B can be selectively disposed only over a received elastic member 332B in a spider-type configuration, or can be disposed around the circumference of the base 310B.

Figure 3C:
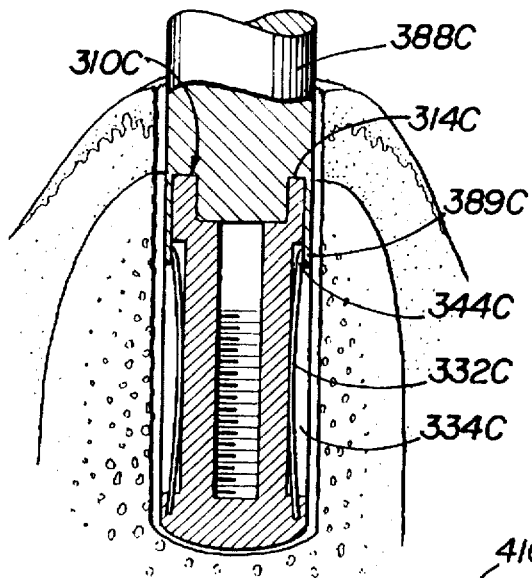

In another embodiment shown in FIG. 3C, the dental prosthesis also has a tool 388C for inserting said prosthesis into said tissues, said tool 388C having a distal end 389C adapted to be selectively disposed about said received elastic member 332C to selectively maintain said elastic member 332C within said recess 334C during insertion of said prosthesis into said tissues. The tool 388C therefore provides a positioning force to the anchoring base 310C by pressure directed to the top 314C. The distal end 389C of the tool 388C can be adapted to cover the extending top end 344C of the elastic member 332C, as shown, or to maintain within the recess 334C any elastic member configuration, such as those shown in FIGS. 2A–2C. The distal end 389C can also be adapted with notches or end hooks to assist in attaching the tool to the elastic member 332C and maintaining it within the recess 334C. The distal end 389C can alternatively be adapted so as to wrap around the circumference of the top 314C of the base 310C.

Figure 3D:
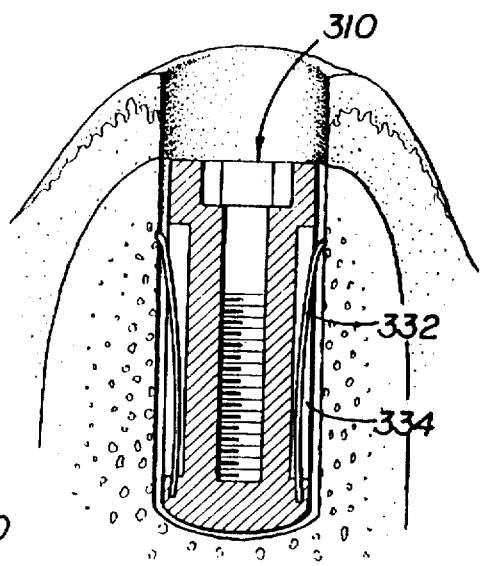
FIG. 3D is a partial cross-section views showing the dental implant within the tissue site with the stabilizing elastic members extended.

FIG. 3D shows the anchoring base 310 implanted in a prepared tissue site with the elastic members 332 extended to stabilize the dental implant.

In those embodiments employing biodegradable polymeric material, it is possible to introduce bioactive chemical agents, or medicaments, into the biodegradable materials so that bioactive agents may be controllably released into the fluids and tissues surrounding the implant. Such agents can also be embedded in porous, but non-biodegradable materials. Such agents might be selected to encourage tissue growth (as in the case of bone growth factors), to reduce the risk of infection (as in the case of antibiotics), or to achieve other medical objectives. More than one bioactive agent, or medicament, can be introduced within a single polymeric implant element. Different agents or combinations of agents can be introduced within different polymeric elements of a single implant, in order to achieve specific dose profiles. The techniques for encapsulating a bioactive chemical agent within a polymer matrix in such a way that the agent is released either by diffusion through the matrix, or by decomposition of the matrix, and for controlling the rate and dose profile of such release, are known to those skilled in the art.

As used herein "a" or "an" means one or more than one, depending upon the context within which it is used. The described and other embodiments of the present invention will be apparent to one with skill in the art.

What is claimed is:

1. A dental prosthesis comprising an anchoring base for insertion into prepared osseous tissue, wherein the anchoring base comprises:
   a. a body portion having a top, a bottom, and an outside surface;
   b. means for attaching the top of said anchoring base to a crown portion;
   c. means on the outside surface of said anchoring base for enhancing osteointegration of said tissue to said anchoring base;
   d. an elastic member extending outwardly from the outside surface of said body portion to provide a stabilizing force against said osseous tissue;
   e. a recess in the outside surface of said body portion for selectively receiving said elastic member therein during positioning of said body portion of said dental prosthesis into said dental tissue; and
   f. retention means for selectively maintaining said elastic member within said recess.

2. The dental prosthesis of claim 1, wherein said retention means further comprises a polymer matrix adapted to biodegrade over a predetermined period of time, wherein said polymer matrix is temporarily disposed about said elastic member to temporarily maintain said elastic member received within said recess.

3. The dental prosthesis of claim 2, wherein a bioactive agent is incorporated into the biodegradable polymer matrix so as to be gradually released into the surrounding tissue during biodegradation of the polymer matrix.

4. The dental prosthesis of claim 2, wherein the polymer matrix comprises a biodegradable component selected from the group consisting of polyglycolides, polylactides and polycaprolactones.

5. The dental prosthesis of claim 1, wherein said retention means further comprises a retention pin adapted to be removably disposed about said elastic member to temporarily maintain said elastic member within said recess during insertion of said prosthesis into said tissue.

6. The dental prosthesis of claim 1, further comprising a tool for inserting said prosthesis into said tissue, comprising a distal end adapted to be selectively disposed about said received elastic member to selectively maintain said elastic member within said recess during insertion of said prosthesis into said tissue.

7. The dental prosthesis of claim 1, wherein said elastic member comprises a polymer matrix adapted to biodegrade over a predetermined period of time and the polymer matrix comprises a biodegradable component selected from the group consisting of polyglycolides, polylactides and polycaprolactones.

8. The dental prosthesis of claim 7, wherein a bioactive agent is incorporated into the biodegradable polymer matrix so as to be gradually released into the surrounding tissue during biodegradation of the polymer matrix.

9. The dental prosthesis of claim 1, wherein said elastic member comprises a bottom end and a top end, the bottom end being attached to said body portion and the top end extending outwardly from said body portion.

10. The dental prosthesis of claim 1, wherein said elastic member comprises a bottom end and a top end, the top end being attached to said body portion and the bottom end extending outwardly from said body portion.

11. The dental prosthesis of claim 1, wherein said elastic member comprises a bottom end and a top end and a middle portion, the bottom end being attached to said body portion, the middle portion of the elastic member extending outwardly from said body portion, and the top end extending inwardly toward said body portion.

12. The dental prosthesis of claim 1, wherein said elastic member comprises a bottom end and a top end and a middle portion, the top end being attached to said body portion, the middle portion of the elastic member extending outwardly from said body portion, and the bottom end extending inwardly toward said body portion.

13. The dental prosthesis of claim 1, wherein said attaching means comprises an opening in the top of said body portion adapted to attachably receive a complimentary shaped projection on said crown portion.

14. The dental prosthesis of claim 13, wherein the opening in the top of said body portion is threaded to receive a complimentary thread on the projection on said crown portion such that said crown portion can be removably attached to said anchoring base.

15. A dental prosthesis comprising an anchoring base for insertion into prepared osseous tissue, wherein the anchoring base comprises:
   a. a body portion having a top, a bottom, and an outside surface;
   b. means for attaching the top of said anchoring base to a crown portion;
   c. means on the outside surface of said anchoring base for enhancing osteointegration of said tissue to said anchoring base; and,
   d. an elastic member extending outwardly from the outside surface of said body portion to provide a stabilizing force against said osseous tissue, said elastic member comprising a polymer matrix adapted to biodegrade over a predetermined period of time.

16. The dental prosthesis of claim 15, wherein a bioactive agent is incorporated into the biodegradable polymer matrix so as to be gradually released into the surrounding tissue during biodegradation of the polymer matrix.

17. The dental prosthesis of claim 15, wherein said elastic member comprises a biodegradable component selected from the group consisting of polyglycolides, polylactides and polycaprolactones.

18. The dental prosthesis of claim 15, wherein said elastic member comprises a bottom end and a top end, the bottom end being attached to said body portion and the top end extending outwardly from said body portion.

19. The dental prosthesis of claim 15, wherein said elastic member comprises a bottom end and a top end, the top end being attached to said body portion and the bottom end extending outwardly from said body portion.

20. The dental prosthesis of claim 15, wherein said elastic member comprises a bottom end and a top end and a middle portion, the bottom end being attached to said body portion, the middle portion of the elastic member extending outwardly from said body portion, and the top end extending inwardly toward said body portion.

21. The dental prosthesis of claim 15, wherein said elastic member comprises a bottom end and a top end and a middle portion, the top end being attached to said body portion, the middle portion of the elastic member extending outwardly from said body portion, and the bottom end extending inwardly toward said body portion.

22. The dental prosthesis of claim 15, wherein said attaching means comprises an opening in the top of said body portion adapted to attachably receive a corresponding projection on said crown portion.

23. The dental prosthesis of claim 22, wherein the opening in the top of said body portion is threaded to receive a complimentary thread on the projection on said crown portion such that said crown portion can be removably attached to said anchoring base.

24. The dental prosthesis of claim 15, wherein said body portion of said dental prosthesis further comprises a recess in said outside surface of said body portion for selectively receiving said elastic member therein during positioning of said body portion of said dental prosthesis into said tissue.

25. The dental prosthesis of claim 24, further comprising a retention means for selectively maintaining said elastic member within said corresponding recess.

26. The dental prosthesis of claim 25, wherein said retention means further comprises a polymer matrix adapted to biodegrade over a predetermined period of time, wherein said polymer matrix is temporarily disposed about said elastic member to temporarily maintain said elastic member received within said recess.

27. The dental prosthesis of claim 26, wherein a bioactive agent is incorporated into the biodegradable polymer matrix so as to be gradually released into the surrounding tissue during biodegradation of the polymer matrix.

28. The dental prosthesis of claim 27, wherein said polymer matrix comprises biodegradable component selected from the group consisting of polyglycolides, polylactides and polycaprolactones.

29. The dental prosthesis of claim 25, wherein said retention means further comprises a retention pin adapted to be removably disposed about said received elastic member to temporarily maintain said elastic member within said recess during insertion of said prosthesis into said tissue.

30. The dental prosthesis of claim 25, further comprising a tool for inserting said prosthesis into said tissue, comprising a distal end adapted to be selectively disposed about said received elastic member to selectively maintain said elastic member within said recess during insertion of said prosthesis into said tissue.

* * * * *